(12) United States Patent
Kuruma et al.

(10) Patent No.: US 7,417,737 B2
(45) Date of Patent: *Aug. 26, 2008

(54) METHOD FOR MEASURING SURFACE PLASMON RESONANCE

(75) Inventors: Koji Kuruma, Kanagawa (JP); Hirohiko Tsuzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 369 days.

This patent is subject to a terminal disclaimer.

(21) Appl. No.: 11/000,401

(22) Filed: Dec. 1, 2004

(65) Prior Publication Data

US 2005/0146723 A1 Jul. 7, 2005

(30) Foreign Application Priority Data

Dec. 2, 2003 (JP) ............................. 2003-403040
Dec. 2, 2003 (JP) ............................. 2003-403041

(51) Int. Cl.
*G01N 21/55* (2006.01)
(52) U.S. Cl. ........................................ 356/445
(58) Field of Classification Search ................ None
See application file for complete search history.

(56) References Cited

U.S. PATENT DOCUMENTS

| 6,480,282 | B1 | 11/2002 | Chinowsky et al. |
| 2002/0126290 | A1 | 9/2002 | Naya |
| 2002/0177161 | A1 | 11/2002 | Latov et al. |

FOREIGN PATENT DOCUMENTS

| EP | 1 243 916 A2 | 9/2002 |
| JP | 09-257806 A | 10/1997 |
| JP | 10-267841 A | 10/1998 |
| JP | 2000-065731 A | 3/2000 |
| JP | 2001-255267 A | 9/2001 |
| JP | 2002-131319 A | 5/2002 |
| JP | 2003-194820 A | 7/2003 |
| JP | 2003-302399 A | 10/2003 |
| JP | 2003-329579 A | 11/2003 |
| JP | 2004-325138 A | 11/2004 |
| WO | WO 90-05317 A1 | 5/1990 |
| WO | WO 97-09618 A1 | 3/1997 |
| WO | WO 99/61896 A | 12/1999 |
| WO | WO 01-43875 A1 | 6/2001 |

OTHER PUBLICATIONS

Bothner, et al., "Defining the Molecular Basis of Arf and Hdm2 Interactions", Journal of Molecular Biology, London, GB, 2001, vol. 314, No. 2, pp. 263-277.

*Primary Examiner*—Gregory J Toatley, Jr.
*Assistant Examiner*—Amanda H Merlino
(74) *Attorney, Agent, or Firm*—Sughrue Mion, PLLC

(57) ABSTRACT

An object of the present invention is to suppress the noise width of a reference cell during measurement and the base line fluctuation. The present invention provides a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the meal film; and exchanging the liquid contained in the above flow channel system, wherein the above method is characterized in that a change in surface plasmon resonance is measured in a state where the flow of the liquid has been stopped, after the liquid contained in the above flow channel system has been exchanged.

8 Claims, 1 Drawing Sheet

METHOD FOR MEASURING SURFACE PLASMON RESONANCE

TECHNICAL FIELD

The present invention relates to a method for measuring surface plasmon resonance, and a method for detecting or measuring a substance interacting with a physiologically active substance using the above method.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules. An example of a surface plasmon resonance measurement device is the device described in Japanese Patent Laid-Open (Kokai) No. 2001-330560.

When a specific binding reaction between a physiologically active substance and a test substance is measured, the binding reaction is generally measured by: connecting in series a reference cell, to which a physiologically active substance interacting with a test substance does not bind, with a detection cell, to which a physiologically active substance interacting with a test substance binds; placing the connected cells in a flow channel system; and feeding a liquid through the reference cell and the detection cell, so as to carry out the measurement of the binding reaction. During the measurement, the liquid contained in the above flow channel system is exchanged from a reference liquid containing no test substance to be measured to a sample liquid containing a test substance to be measured, so as to cause the binding reaction between the physiologically active substance and the test substance to be initiated, and to measure a change in signals due to a lapse of time. However, this measurement method is problematic in terms of the noise width of the change in signals of the reference cell during measurement and in terms of base line fluctuation. Thus, it has been difficult to obtain binding detection data with high reliability.

DISCLOSURE OF THE INVENTION

It is an object of the present invention is to solve the aforementioned problems of the prior art techniques. In other words, it is an object of the present invention to suppress the noise width of a reference cell during measurement and the base line fluctuation, when a specific binding reaction between a physiologically active substance and a test substance is measured using a surface plasmon resonance measurement device.

As a result of intensive studies directed towards achieving the aforementioned object, the present inventors have found that when a change in surface plasmon resonance is measured by exchanging the liquid contained in a flow channel system using a surface plasmon resonance measurement device, the aforementioned object can be achieved by exchanging the liquid contained in the above flow channel system, and then measuring the change in surface plasmon resonance in a state where the flow of the liquid has been stopped. Moreover, the present inventors have also found that when a change in surface plasmon resonance is measured by exchanging the liquid contained in a flow channel system using a surface plasmon resonance measurement device, the ratio (Ve/Vs) of the amount of a liquid exchanged (Ve ml) in a single measurement to the volume of a cell (Vs ml) is adjusted between 1 and 100, so as to achieve the aforementioned object. The present invention has been completed based on these findings.

That is to say, the first embodiment of the present invention provides a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the meal film; and exchanging the liquid contained in the above flow channel system, wherein the above method is characterized in that a change in surface plasmon resonance is measured in a state where the flow of the liquid has been stopped, after the liquid contained in the above flow channel system has been exchanged.

Preferably, the present invention provides a method for measuring a change in surface plasmon resonance, which comprises: using a surface plasmon resonance measurement device comprising a dielectric block, a metal film formed on one side of the dielectric block, a light source for generating a light beam, an optical system for allowing the above light beam to enter the above dielectric block so that total reflection conditions can be obtained at the interface between the dielectric block and the metal film and so that various incidence angles can be included, a flow channel system comprising a cell formed on the above metal film, and a light-detecting means for detecting the state of surface plasmon resonance by measuring the intensity of the light beam totally reflected at the above interface, and exchanging the liquid contained in the above flow channel system, wherein the above method is characterized in that a change in surface plasmon resonance is measured in a state where the flow of the liquid has been stopped, after the liquid contained in the above flow channel system has been exchanged.

Preferably, the liquid contained in the above flow channel system is exchanged from a reference liquid containing no test substance to be measured to a sample liquid containing a test substance to be measured, and thereafter, a change in surface plasmon resonance is measured in a state where the flow of the sample liquid has been stopped.

Preferably, a reference cell, to which a physiologically active substance interacting with a test substance does not bind, is connected in series with a detection cell, to which a physiologically active substance interacting with a test substance binds, the connected cells are placed in a flow channel system, and a liquid is then fed through the reference cell and the detection cell.

Preferably, the ratio (Ve/Vs) of the amount of a liquid exchanged (Ve ml) in a single measurement to the volume of the above cell (Vs ml) is between 1 and 100, and more preferably the ratio (Ve/Vs) is between 1 and 50.

Preferably, the time required for the exchange of the liquid contained in the above flow channel system is between 0.01 second and 100 seconds.

In another aspect, the present invention provides a method for detecting or measuring a substance interacting with a physiologically active substance, which comprises steps of: using at least a single cell, to the surface of which a physiologically active substance binds by covalent bonding; allowing a sample liquid containing a test substance to be measured to come into contact with the above cell; and measuring a change in surface plasmon resonance by the aforementioned method of the present invention.

The second embodiment of the present invention provides a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the meal film; and exchanging the liquid contained in the above flow channel system, wherein the above method is characterized in that the ratio (Ve/Vs) of the amount of a liquid exchanged (Ve ml) in a single measurement to the volume of the above cell (Vs ml) is between 1 and 100.

Preferably, the present invention provides a method for measuring a change in surface plasmon resonance, which comprises: using a surface plasmon resonance measurement device comprising a dielectric block, a metal film formed on one side of the dielectric block, a light source for generating a light beam, an optical system for allowing the above light beam to enter the above dielectric block so that total reflection conditions can be obtained at the interface between the dielectric block and the metal film and so that various incidence angles can be included, a flow channel system comprising a cell formed on the above metal film, and a light-detecting means for detecting the state of surface plasmon resonance by measuring the intensity of the light beam totally reflected at the above interface, and exchanging the liquid contained in the above flow channel system, wherein the above method is characterized in that the ratio (Ve/Vs) of the amount of a liquid exchanged (Ve ml) in a single measurement to the volume of the above cell (Vs ml) is between 1 and 100.

Preferably, the liquid contained in the above flow channel system is exchanged from a reference liquid containing no test substance to be measured to a sample liquid containing a test substance to be measured.

Preferably, a reference cell, to which a physiologically active substance interacting with a test substance does not bind, is connected in series with a detection cell, to which a physiologically active substance interacting with a test substance binds, the connected cells are placed in a flow channel system, and a liquid is then fed through the reference cell and the detection cell.

Preferably, the ratio (Ve/Vs) of the amount of a liquid exchanged (Ve ml) in a single measurement to the volume of the above cell (Vs ml) is between 1 and 50.

Preferably, the time required for the exchange of the liquid contained in the above flow channel system is between 0.01 second and 100 seconds.

Preferably, after the liquid contained in the above flow channel system has been exchanged, a change in surface plasmon resonance can be measured in a state where the flow of the liquid has been stopped.

In another aspect, the present invention provides a method for detecting or measuring a substance interacting with a physiologically active substance, which comprises steps of: using at least a single cell, to the surface of which a physiologically active substance binds by covalent bonding; allowing a sample liquid containing a test substance to be measured to come into contact with the above cell; and measuring a change in surface plasmon resonance by the aforementioned method of the present invention.

Figure 1:
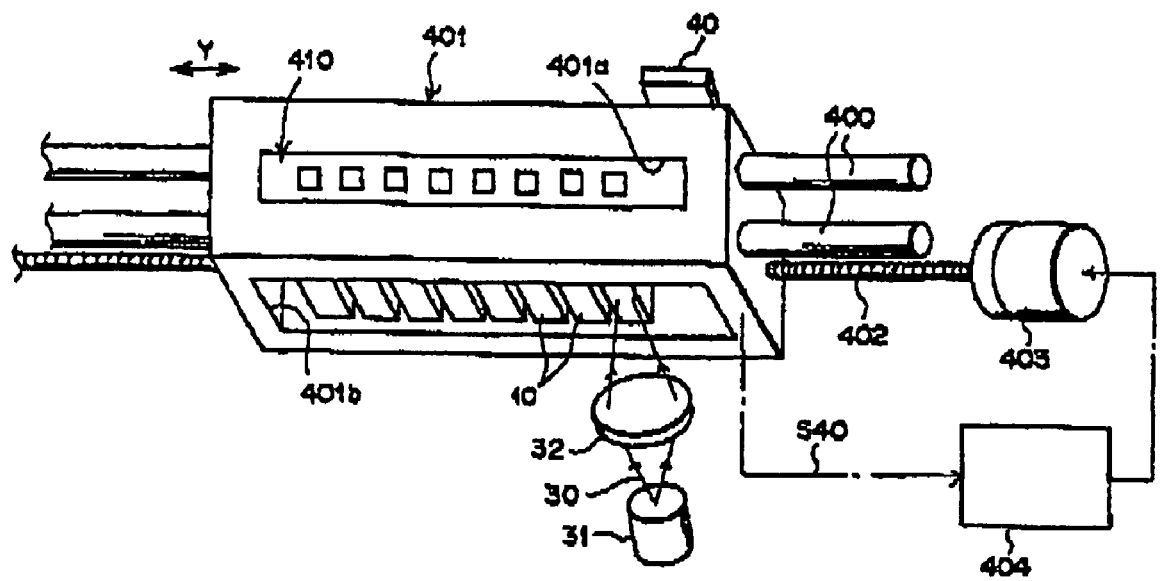
FIG. 1 shows a surface plasmon resonance measurement device.

In figures, 10 indicates measurement unit, 11 indicates dielectric block, 12 indicates metal film, 13 indicates sample-retaining frame, 14 indicates sensing substance, 31 indicates laser light source, 32 indicates condenser lens, 40 indicates light detector, S40 indicates output signal, 400 indicates guide rod, 401 indicates slide block, 402 indicates precision screw, 403 indicates pulse motor, 404 indicates motor controller, 410 indicates unit connector, and 411 indicates connecting member.

BEST MODE FOR CARRYING OUT THE INVENTION

The embodiments of the present invention will be described below.

The first embodiment of the present invention relates to a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the meal film; and exchanging the liquid contained in the above flow channel system, wherein the above method is characterized in that a change in surface plasmon resonance is measured in a state where the flow of the liquid has been stopped, after the liquid contained in the above flow channel system has been exchanged.

The second embodiment of the present invention relates to a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the meal film; and exchanging the liquid contained in the above flow channel system, wherein the above method is characterized in that the ratio (Ve/Vs) of the amount of a liquid exchanged (Ve ml) in a single measurement to the volume of the above cell (Vs ml) is between 1 and 100.

In the first embodiment of the present invention, the noise width of a change in signals of a reference cell during measurement and base line fluctuation can be suppressed by measuring a change in surface plasmon resonance in a state where the flow of a liquid has been stopped, so that binding detection data with high reliability can be obtained for the first time. The time of the stop of the flow of the liquid is not particularly limited. For example, it may be between 1 second and 30 minutes, preferably between 10 seconds and 20 minutes, and more preferably between 1 minute and 20 minutes.

In the second embodiment of the present invention, the noise width of a change in signals of a reference cell during measurement and base line fluctuation can be suppressed by adjusting the ratio (Ve/Vs) of the amount of a liquid exchanged (Ve ml) in a single measurement to the volume (Vs ml) of a cell between 1 and 100, so that binding detection data with high reliability can be obtained for the first time.

In the present invention, preferably, the liquid contained in a flow channel system is exchanged from a reference liquid containing no test substance to be measured to a sample liquid containing a test substance to be measured, and thereafter, a change in surface plasmon resonance can be measured in a state where the flow of the sample liquid has been stopped.

In the present invention, preferably, a reference cell, to which a substance interacting with a test substance does not bind, is connected in series with a detection cell, to which a substance interacting with a test substance binds, the connected cells are placed in a flow channel system, and a liquid is then fed through the reference cell and the detection cell, so that a change in surface plasmon resonance can be measured.

In addition, in the present invention, the ratio (Ve/Vs) of the amount of a liquid exchanged (Ve ml) in a single measurement to the volume (Vs ml) of a cell used in measurement (and when the aforementioned reference cell and detection cell are used, the total volume of these cells) is preferably between 1 and 100. Ve/Vs is more preferably between 1 and 50, and particularly preferably between 1 and 20. The volume (Vs ml) of a cell used in measurement is not particularly limited. It is preferably between $1\times10^{-6}$ and 1.0 ml, and particularly preferably between $1\times10^{-5}$ and $1\times10^{-1}$ ml.

The period of time necessary for exchanging the liquid is preferably between 0.01 second and 1,000 seconds, more preferably between 0.1 second and 800 seconds, and further more preferably between 0.01 second and 100 seconds, and particularly preferably between 0.1 second and 10 seconds.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light. The surface plasmon resonance measurement device used in the present invention will be described below.

The surface plasmon resonance measurement device is a device for analyzing the properties of a substance to be measured using a phenomenon whereby a surface plasmon is excited with a lightwave. The surface plasmon resonance measurement device used in the present invention comprises a dielectric block, a metal film formed on a face of the dielectric block, a light source for generating a light beam, an optical system for allowing the above light beam to enter the above dielectric block such that total reflection conditions can be obtained at the interface between the above dielectric block and the above metal film and that components at various incident angles can be contained, and a light-detecting means for detecting the state of surface plasmon resonance by measuring the intensity of the light beam totally reflected at the above interface.

Moreover, as stated above, the above dielectric block is formed as one block comprising the entity of the entrance face and exit face of the above light beam and a face on which the above metal film is formed, and the above metal film is integrated with this dielectric block.

In the present invention, more specifically, a surface plasmon resonance measurement device shown in FIGS. 1 to 32 of Japanese Patent Laid-Open No. 2001-330560, and a surface plasmon resonance device shown in FIGS. 1 to 15 of Japanese Patent Laid-Open No. 2002-296177, can be preferably used. All of the contents as disclosed in Japanese Patent Laid-Open Nos. 2001-330560 and 2002-296177 cited in the present specification are incorporated herein by reference as a part of the disclosure of this specification.

For example, the surface plasmon resonance measurement device described in Japanese Patent Laid-Open No. 2001-330560 is characterized in that it comprises: a dielectric block; a thin metal film formed on a face of the dielectric block; multiple measurement units comprising a sample-retaining mechanism for retaining a sample on the surface of the thin film; a supporting medium for supporting the multiple measurement units; a light source for generating a light beam; an optical system for allowing the above light beam to enter the dielectric block at various angles so that total reflection conditions can be obtained at the interface between the dielectric block and the metal film; a light-detecting means for measuring the intensity of the light beam totally reflected at the above interface and detecting the state of attenuated total reflection caused by surface plasmon resonance; and a driving means for making the above supporting medium, the above optical system and the above light-detecting means move relative to one another, and successively placing each of the above multiple measurement units in a certain position appropriate to the above optical system and the above light-detecting means, so that the above total reflection conditions and various incident angles can be obtained with respect to each dielectric block of the above multiple measurement units.

It is to be noted that in the above measurement device, the above optical system and light-detecting means are kept in a resting state and the above driving means makes the above supporting medium move.

In such a case, the above supporting medium is desirably a turntable for supporting the above multiple measurement units on a circle centered on a rotation axis, and the above driving means is desirably a means for intermittently rotating this turntable. In this case, a medium for supporting the above multiple measurement units that are linearly arranged in a line may be used as the above supporting medium, and a means that makes such a supporting medium move linearly in an intermittent fashion in the direction in which the above multiple measurement units are arranged may be applied as the above driving means.

Otherwise, on the contrary, it may also be possible that the above supporting medium be retained in a resting state and that the above driving means makes the above optical system and light-detecting means move.

In such a case, the above supporting medium is desirably a medium for supporting the above multiple measurement units on a circle, and the above driving means is desirably a means for intermittently rotating the above optical system and light-detecting means along the multiple measurement units supported by the above supporting medium. In this case, a medium for supporting the above multiple measurement units that are linearly arranged in a line may be used as the above supporting medium, and a means that makes the above optical system and light-detecting means move linearly in an intermittent fashion along the multiple measurement units supported by the above supporting medium may be applied as the above driving means.

Otherwise, when the above driving means has a tolling bearing that supports a rotation axis, the driving means is desirably configured such that after the rotation axis has been rotated to a certain direction and a series of measurements for the above multiple measurement units has been terminated, the above rotation axis is equivalently rotated to the opposite direction, and then it is rotated again to the same above direction for the next series of measurements.

In addition, the above-described measurement device is desirably configured such that the above multiple measurement units are connected in a line with a connecting member so as to constitute a unit connected body and that the above supporting medium supports the unit connected body.

Moreover, in the above-described measurement device, it is desirable to establish a means for automatically feeding a given sample to each sample-retaining mechanism of the multiple measurement units supported by the above supporting medium.

Furthermore, in the above-described measurement device, it is desirable that the dielectric block of the above measurement unit be immobilized to the above supporting medium, that a thin film layer and a sample-retaining mechanism of the measurement unit be unified so as to constitute a measurement chip, and that the measurement chip be formed such that it is exchangeable with respect to the above dielectric block.

When such a measurement chip is applied, it is desirable to establish a cassette for accommodating a multiple number of the measurement chips and a chip-supplying means for successively taking a measurement chip out of the cassette and supplying it in a state in which it is connected to the above dielectric block.

Otherwise, it may also be possible to unify the dielectric block of the measurement unit, the thin film layer and the sample-retaining mechanism, so as to constitute a measurement chip, and it may also be possible for this measurement chip to be formed such that it is exchangeable with respect to the above supporting medium.

When a measurement chip has such a structure, it is desirable to establish a cassette for accommodating a multiple number of measurement chips and a chip-supplying means for successively taking a measurement chip out of the cassette and supplying it in a state in which it is supported by the supporting medium.

The above optical system is desirably configured such that it makes a light beam enter the dielectric block in a state of convergent light or divergent light. Moreover, the above light-detecting means is desirably configured such that it detects the position of a dark line generated due to attenuated total reflection, which exists in the totally reflected light beam, Furthermore, the above optical system is desirably configured such that it makes a light beam enter the above interface in a defocused state. In this case, the beam diameter of the light beam at the above interface in a direction wherein the above supporting medium moves is desirably ten times or greater the mechanical positioning precision of the above supporting medium.

Still further, the above-described measurement device is desirably configured such that the measurement unit is supported on the upper side of the above supporting medium, such that the above light source is placed so as to project the above light beam from a position above the above supporting medium to downwards, and such that the above optical system comprises a reflecting member for reflecting upwards the above light beam projected to downwards as described above and making it proceed towards the above interface.

Still further, the above-described measurement device is desirably configured such that the above measurement unit is supported on the upper side of the above supporting medium, such that the above optical system is constituted so as to make the above light beam enter the above interface from the downside thereof, and such that the above light-detecting means is placed in a position above the above supporting medium with a light-detecting plane thereof facing downwards, as well as comprising a reflecting member for reflecting upwards the totally reflected light beam at the above interface and making it proceed towards the above light-detecting means.

What is more, the above-described measurement device desirably comprises a temperature-controlling means for maintaining the temperature of the above measurement unit before and/or after being supported by the above supporting medium at a predetermined temperature.

Moreover, the above-described measurement device desirably comprises a means for stirring the sample stored in the sample-retaining mechanism of the measurement unit supported by the above supporting medium before detecting the state of attenuated total reflection as mentioned above.

Furthermore, in the above-described measurement device, it is desirable to establish in at least one of the multiple measurement units supported by the above supporting medium a standard solution-supplying means for supplying a standard solution having optical properties associated with the optical properties of the above sample, as well as a correcting means for correcting data regarding the above attenuated total reflection state of the sample based on the data regarding the above attenuated total reflection state of the above standard solution.

In such a case, if the sample is obtained by dissolving a test substance in a solvent, it is desirable that the above standard solution-supplying means be a means for supplying the above solvent as a standard solution.

Still further, the above measurement device desirably comprises: a mark for indicating individual recognition information; a reading means for reading the above mark from the measurement unit used in measurement; an inputting means for inputting sample information regarding the sample supplied to the measurement unit; a displaying means for displaying measurement results; and a controlling means connected to the above displaying means, inputting means and reading means, which stores the above individual recognition information and sample information of each measurement unit while associating them with each other, as well as making the above displaying means display the measurement results of the sample retained in a certain measurement unit while associating them with the above individual recognition information and sample information of each measurement unit.

When a substance interacting with a physiologically active substance is detected or measured using the above-described measurement device, a state of attenuated total reflection is detected in a sample contained in one of the above measurement units, and thereafter, the above supporting medium, optical system and light-detecting means are moved relative to one another, so that a state of attenuated total reflection is detected in a sample contained in another measurement unit. Thereafter, the above supporting medium, optical system and light-detecting means are again moved relative to one another, so that a state of attenuated total reflection is detected again the sample contained in the above one measurement unit, thereby completing the measurement.

The measurement chip used in the present invention is used for the surface plasmon resonance measurement device having a structure described herein, and comprises a dielectric block and a metal film formed on a face of the dielectric block, in which the dielectric block is formed as one block comprising the entirety of the entrance face and exit face of the light beam and a face on which the above metal film is formed, the above metal film is integrated with the above dielectric block.

A metal constituting the metal film is not particularly limited, as long as surface plasmon resonance is generated. Examples of a preferred metal may include free-electron metals such as gold, silver, copper, aluminum or platinum, Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 1 angstrom and 5,000 angstroms, and particularly preferably between 10 angstroms and 2,000 angstroms. If the thickness exceeds 5,000 angstroms, the surface plasmon phenomenon of a medium cannot be sufficiently detected. Moreover, when an interstitial layer consisting of chrome or the like is provided, the thickness of the interstitial layer is preferably between 1 angstrom and 100 angstroms.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

Preferably, the metal film has a functional group capable of immobilizing a physiologically active substance on the outermost surface of the substrate. The term "the outermost surface of the substrate" is used to mean "the surface, which is farthest from the substrate".

Examples of a preferred functional group may include —H, —SH, —COOH, —NR$^1$R$^2$ (wherein each of R$^1$ and R$^2$ independently represents a hydrogen atom or lower alkyl group), —CHO, —NR$^3$NR$^1$R$^2$ (wherein each of R$^1$, R$^2$ and R$^3$ independently represents a hydrogen atom or lower alkyl group), —NCO, —NCS, an epoxy group, and a vinyl group. The number of carbon atoms contained in the lower alkyl group is not particularly limited herein. However, it is generally about C1 to C10, and preferably C1 to C6.

Examples of the method of introducing such a functional group include a method which involves applying a polymer containing a precursor of such a functional group on a metal surface or metal film, and then generating the functional group from the precursor located on the outermost surface by chemical treatment.

In the measurement chip obtained as mentioned above, a physiologically active substance is covalently bound thereto via the above functional group, so that the physiologically active substance can be immobilized on the metal film.

A physiologically active substance immobilized on the surface for the measurment chip of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanarycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme, or nucleic acid, an amino group, thiol group or the like of the physiologically active substance is covalently bound to a functional group located on a metal surface, so that the physiologically active substance can be immobilized on the metal surface.

A measurement chip to which a physiologically active substance is immobilized as described above can be used to detect and/or measure a substance which interacts with the physiologically active substance.

Namely, the present invention provides a method for detecting or measuring a substance interacting with a physiologically active substance, which comprises steps of: using at least a measurement chip (cell), to the surface of which a physiologically active substance binds by covalent bonding; allowing a sample liquid containing a test substance to be measured to come into contact with the above cell; and after exchanging the liquid contained in a flow channel system, measuring a change in surface plasmon resonance in a state where the flow of the liquid has been stopped.

Further, the present invention provides a method for detecting or measuring a substance interacting with a physiologically active substance, which comprises steps of: using at least a measurement chip (cell), to the surface of which a physiologically active substance binds by covalent bonding; allowing a sample liquid containing a test substance to be measured to come into contact with the above cell; exchanging the liquid contained in a flow channel system under the condition that the ratio (Ve/Vs) of the amount of a liquid exchanged (Ve ml) in a single measurement to the volume of the above cell (Vs ml) is between 1 and 100, and measuring a change in surface plasmon resonance.

As a test substance, a sample containing a substance interacting with the aforementioned physiologically active substance can be used, for example.

EXAMPLES

The following experiment was carried out using a device shown in FIG. 22 of Japanese Patent Laid-Open No. 2001-330560 (hereinafter referred to as the surface plasmon resonance measurement device of the present invention) (shown in FIG. 1 of the present specification) and a dielectric block shown in FIG. 23 of Japanese Patent Laid-Open No. 2001-330560 (hereinafter referred to as the dielectric block of the present invention) (shown in FIG. 2 of the present specification).

In the surface plasmon resonance measurement device shown in FIG. 1, a slide block 401 is used as a supporting medium for supporting measurement units, which is joined to two guide rods 400, 400 placed in parallel with each other while flexibly sliding in contact, and which also flexibly moves linearly along the two rods in the direction of an arrow Y in the figure. The slide block 401 is screwed together with a precision screw 402 placed in parallel with the above guide rods 400, 400, and the precision screw 402 is reciprocally rotated by a pulse motor 403 which constitutes a supporting medium-driving means together with the precision screw 402.

It is to be noted that the movement of the pulse motor 403 is controlled by a motor controller 404. This is to say, an output signal S 40 of a linear encoder (not shown in the figure), which is incorporated into the slide block 401 and detects the position of the slide block 401 in the longitudinal direction of the guide rods 400, 400, is inputted into the motor controller 404. The motor controller 404 controls the movement of the pulse motor 403 based on the signal S 40.

Moreover, below the guide rods 400, 400, there are established a laser light source 31 and a condenser 32 such that they sandwich from both sides the slide block 401 moving along the guide rods, and a photodetector 40. The condenser 32 condenses a light beam 30. In addition, the photodetector 40 is placed thereon.

In this embodiment, a stick-form unit connected body 410 obtained by connecting and fixing eight measurement units 10 is used as an example, and the measurement units 10 are mounted on the slide block 401 in a state in which eight units are arranged in a line.

Figure 2:
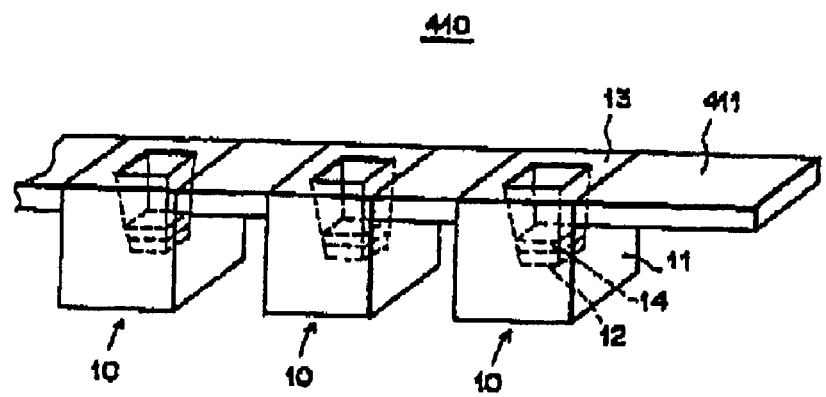
FIG. 2 shows a dielectric block.

FIG. 2 shows the structure of the unit connected body 410 in detail. As shown in the figure, the unit connected body 410 is obtained by connecting the eight measurement units 10 by a connecting member 411.

This measurement unit 10 is obtained by molding a dielectric block 11 and a sample-retaining frame 13 into one piece, for example, using transparent resin or the like. The measurement unit constitutes a measurement chip that is exchangeable with respect to a turntable. In order to make the measurement chip exchangeable, for example, the measurement unit 10 may be fitted into a through-hole that is formed in the turntable. In the present example, a sensing substance 14 is immobilized on a metal film 12.

Example 1

(1) Production of Dextran Measurement Chip

The dielectric block of the present invention, onto which gold having a thickness of 50 nm had been evaporated as a metal film, was treated with a Model-208 UV-ozone cleaning system (TECHNOVISION INC.) for 30 minutes. Thereafter, 5.0 mM solution containing 11-hydroxy-1-undecanethiol in ethanol/water (80/20) was added to the metal film such that it came into contact with the metal film, followed by a surface treatment at 25° C. for 18 hours. Thereafter, the resultant product was washed with ethanol 5 times, with a mixed solvent consisting of ethanol and water 1 time, and then with water 5 times.

Subsequently, the surface coated with 11-hydroxy-1-undecanethiol was allowed to come into contact with 10% by weight of epichlorohydrin solution (solvent: a mixed solution consisting of 0.4 M sodium hydroxide and diethylene glycol dimethyl ether at a ratio of 1:1), and a reaction was then carried out in a shaking incubator at 25° C. for 4 hours. Thereafter, the surface was washed with ethanol 2 times, and then with water 5 times.

Subsequently, 4.5 ml of 1 M sodium hydroxide was added to 40.5 ml of 25% by weight of dextran (T500, Pharmacia) aqueous solution. The obtained solution was allowed to come into contact with the surface treated with epichlorohydrin. The surface was then incubated in a shaking incubator at 25° C. for 20 hours. Thereafter, the resultant surface was washed with 50° C. water 10 times.

Subsequently, a mixture obtained by dissolving 3.5 g of bromoacetic acid in 27 g of a 2 M sodium hydroxide solution was allowed to come into contact with the above dextran-treated surface, and the obtained surface was then incubated in a shaking incubator at 28° C. for 16 hours. The surface was washed with water. Thereafter, the above-describe procedure was repeated once.

(2) Production of Trypsin-immobilized Chip

The solution in the above-describe dextran measurement chip was removed therefrom. Thereafter, 70 μl of a mixed solution consisting of 200 mM EDC (N-ethyl-N'-(3-dimethylaminopropyl)carbodiimide hydrochloride) and 50 mM NHS (N-hydroxysuccinimide) was added to the measurement chip, and it was then left for 10 minutes. The mixed solution was removed from the measurement chip, and the chip was then washed with 100 μl of water 3 times, and then with 100 μl of buffer 1 (100 mM HEPES (N-2-hydroxyethylpiperazin-N'-2-ethanesulfonic acid), 150 mM NaCl, 10 mM CaCl$_2$) 3 times. The chip containing 100 μl of buffer 1 was installed in the surface plasmon resonance measurement device of the present invention. The inside of the chip was replaced with a trypsin solution (produced by dissolving trypsin in buffer 1 to a concentration of 1 mg/ml), and it was then left for 30 minutes, so as to immobilize trypsin. Thereafter, the inside of the chip was replaced with a 1 M ethanolamine solution, and it was then left for 10 minutes. Thereafter, the inside of the chip was washed with 100 μl of buffer 1 ten times. The amount of a change in resonance signals due to immobilization of trypsin was 2,000 RU.

(3) Production of Reference Chip

The solution in the above-described dextran measurement chip was removed therefrom. Thereafter, 70 μl of a mixed solution consisting of 200 mM EDC and 50 mM NHS was added to the measurement chip, and it was then left for 10 minutes. Thereafter, the mixed solution was removed from the measurement chip, and the chip was then washed with 100 μl of water 3 times, and then with 100 μl of buffer 1 three times. The inside of the chip was replaced with a 1 M ethanolamine solution, and it was then left for 10 minutes. Thereafter, the inside of the chip was washed with 100 μl of buffer 1 ten times.

(4) Production of Flow Channel System

With regard to the trypsin-immobilized chip of the present invention, the dielectric block was capped with silicon rubber, so as to produce a cell with an internal volume of 15 μl. In the case of such a block cell, the volume of the cell is determined with a space surrounded by the measurement chip and the cap. Two holes each having a diameter of 1 mm were formed through the silicon rubber used as a cap, and a Teflon tube having an inside diameter of 0.5 mm and an outside diameter of 1 mm was passed through each of these holes, so as to produce a flow channel. Likewise, a cap and a flow channel were produced for a reference chip. Thereafter, the two chips were connected in series, so as to produce a flow channel system. Each of the two chips in this flow channel system was installed in the surface plasmon resonance measurement device of the present invention.

(5) Evaluation of Leupeptin-binding Ability

The inside of the flow channel system was filled with buffer 2 (10 mM HEPES, 150 mM NaCl). Defining the state before the exchange of the liquid as a standard, a change in signals was measured at intervals of 0.5 seconds. The inside of the flow channel system was replaced with a leupeptin solution produced by dissolving leupeptin in buffer 2 to a concentration of 1 μg/ml) by each method described in Table 1. The level of noise generated on the reference chip side at 2 to 10 minutes after initiation of the replacement, and changes in signals on the trypsin-immobilized chip side and on the reference chip side at 10 minutes after initiation of the replacement, are shown in Table 1. In order to obtain binding detection data with high reliability, it is preferable that the width of noise level (the difference between the maximum and the minimum in a change in signals) be within 10 RU, and that the base line fluctuation, that is, the change in signals on the reference chip side be within 10 RU. More preferably, the above values are both within 5 RU.

TABLE 1

| | Liquid exchange method | | | | | | | | | |
| | | Exchange time | | | Amount of liquid | Cell | | Noise width | Signal change | | |
| No. | Flow rate (ml/min) | (min) | (In terms of sec) | Termination time (min) | exchanged (Ve) (ml) | volume (Vs) (ml)* | Ve/Vs | of reference chip (RU) | Immobilized chip (RU) | Reference chip (RU) | Remarks |
|---|---|---|---|---|---|---|---|---|---|---|---|
| 1 | 4 | 0.125 | 7.5 | 9.875 | 0.5 | 0.03 | 16.7 | 3 | 19 | 1 | Example |
| 2 | 4 | 0.25 | 15 | 9.75 | 1 | 0.03 | 33.3 | 3 | 21 | 2 | Example |
| 3 | 4 | 1 | 60 | 9 | 4 | 0.03 | 133.3 | 5 | 20 | 2 | Example |
| 4 | 4 | 1.5 | 90 | 8.5 | 6 | 0.03 | 200.0 | 8 | 21 | 2 | Example |
| 5 | 4 | 10 | 600 | 0 | 40 | 0.03 | 1333.3 | 48 | 12 | 12 | Comparative example |
| 6 | 2 | 10 | 600 | 0 | 20 | 0.03 | 666.7 | 41 | 25 | 7 | Comparative example |
| 7 | 1 | 10 | 600 | 0 | 10 | 0.03 | 333.3 | 25 | 18 | 10 | Comparative example |
| 8 | 0.5 | 10 | 600 | 0 | 5 | 0.03 | 166.7 | 16 | 26 | 6 | Comparative example |

*15 μl (volume per cell) × 2

From the results shown in Table 1, it was found that using the measurement methods of the present invention (Nos. 1 to 4 in Table 1), highly reliable measurement results with a low noise level (the noise width of the reference chip) and small base line fluctuation (the change in signals of the reference chip) could be obtained.

Example 2

The same operations as described in (1) to (4) in Example 1 were carried out.

(5) Evaluation of Leupeptin-binding Ability

The inside of the flow channel system was filled with buffer 2 (10 mM HBPES, 150 mM NaCl). Defining the state before the exchange of the liquid as a standard, a change in signals was measured at intervals of 0.5 seconds. The inside of the flow channel system was replaced with a leupeptin solution (produced by dissolving leupeptin in buffer 2 to a concentration of 1 μg ml) by each method described in Table 2. The level of noise generated on the reference chip side at 2 to 10 minutes after initiation of the replacement, and changes in signals on the trypsin-immobilized chip side and on the reference chip side at 10 minutes after initiation of the replacement, are shown in Table 2. In order to obtain binding detection data with high reliability, it is preferable that the width of noise level (the difference between the maximum and the minimum in a change in signals) be within 10 RU, and that the base line fluctuation, that is, the change in signals on the reference chip side be within 10 RU. More preferably, the above values are both within 5 RU.

TABLE 2

| | Liquid exchange method | | | | | | | | | |
|---|---|---|---|---|---|---|---|---|---|---|
| | Exchange time | | | Amount of liquid | Cell | | | Noise width | Signal change | |
| No. | Flow rate (ml/min) | (min) | (In terms of sec) | Termination time (min) | exchanged (Ve) (ml) | volume (Vs) (ml)* | $Ve/V_s$ | of reference chip (RU) | Immobilized chip (RU) | Reference chip (RU) | Remarks |
| 1 | 4 | 0.125 | 7.5 | 9.875 | 0.5 | 0.03 | 16.7 | 3 | 19 | 1 | Example |
| 2 | 4 | 0.25 | 15 | 9.75 | 1 | 0.03 | 33.3 | 3 | 21 | 2 | Example |
| 3 | 4 | 10 | 600 | 0 | 40 | 0.03 | 1333.3 | 48 | 12 | 12 | Comparative example |
| 4 | 2 | 10 | 600 | 0 | 20 | 0.03 | 666.7 | 41 | 25 | 7 | Comparative example |
| 5 | 1 | 10 | 600 | 0 | 10 | 0.03 | 333.3 | 25 | 18 | 10 | Comparative example |
| 6 | 0.5 | 10 | 600 | 0 | 5 | 0.03 | 166.7 | 16 | 26 | 6 | Comparative example |
| 7 | 0.2 | 10 | 600 | 0 | 2 | 0.03 | 66.7 | 9 | 22 | 4 | Example |
| 8 | 0.1 | 10 | 600 | 0 | 1 | 0.03 | 33.3 | 6 | 20 | 3 | Example |

*15 μl (volume per cell) × 2

From the results shown in Table 2, it was found that using the measurement methods of the present invention (Nos. 1, 2, 7, and 8 in Table 2), highly reliable measurement results with a low noise level (the noise width of the reference chip) and a small base line fluctuation (the change in signals of the reference chip) could be obtained.

EFFECTS OF THE INVENTION

The measurement method of the present invention enables the achievement of highly reliable measurement results with a low noise level (the noise width of the reference chip) and small base line fluctuation (the change in signals of the reference chip).

The invention claimed is:

1. A method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the metal film; and exchanging the liquid contained in the above flow channel system, wherein the above method is characterized in that a change in surface plasmon resonance is measured in a state where the flow of the liquid has been stopped, after the liquid contained in the above flow channel system has been exchanged.

2. A method for measuring a change in surface plasmon resonance, which comprises: using a surface plasmon resonance measurement device comprising a dielectric block, a metal film formed on one side of the dielectric block, a light source for generating a light beam, an optical system for allowing the above light beam to enter the above dielectric block so that total reflection conditions can be obtained at the interface between the dielectric block and the metal film and so that various incidence angles can be included, a flow channel system comprising a cell formed on the above metal film, and a light-detecting means for detecting the state of surface plasmon resonance by measuring the intensity of the light beam totally reflected at the above interface, and exchanging the liquid contained in the above flow channel system, wherein the above method is characterized in that a change in surface plasmon resonance is measured in a state where the flow of the liquid has been stopped, after the liquid contained in the above flow channel system has been exchanged.

3. The method for measurement according to claim 1 wherein the liquid contained in the above flow channel system is exchanged from a reference liquid containing no test substance to be measured to a sample liquid containing a test substance to be measured, and thereafter, a change in surface plasmon resonance is measured in a state where the flow of the sample liquid has been stopped.

4. The method for measurement according to claim 1 wherein a reference cell, to which a physiologically active substance interacting with a test substance does not bind, is connected in series with a detection cell, to which a physiologically active substance interacting with a test substance binds, the connected cells are placed in a flow channel system, and a liquid is then fed through the reference cell and the detection cell.

5. The method for measurement according to claim 1 wherein the ratio (Ve/Vs) of the amount of a liquid exchanged (Ve ml) in a single measurement to the volume of the above cell (Vs ml) is between 1 and 100.

6. The method for measurement according to claim 5 wherein the ratio (Ve/Vs) is between 1 and 50.

7. The method for measurement according to claim 1 wherein the time required for the exchange of the liquid contained in the above flow channel system is between 0.01 second and 100 seconds.

8. A method for detecting or measuring a substance interacting with a physiologically active substance, which comprises steps of: using at least a single cell, to the surface of which a physiologically active substance binds by covalent bonding; allowing a sample liquid containing a test substance to be measured to come into contact with the above cell; and measuring a change in surface plasmon resonance by the method according to claim 1.

* * * * *